(12) United States Patent
Grinter et al.

(10) Patent No.: US 8,263,611 B2
(45) Date of Patent: Sep. 11, 2012

(54) HYDROCHLORIDE SALT OF AN AZABICYCLO[3.2.1]OCTANE DERIVATIVE

(75) Inventors: Trevor John Grinter, Kent (GB); Peter Moldt, Rungsted Kyst (DK); Frank Watjen, Farum (DK)

(73) Assignee: Neurosearch A/S, Ballerup (DK)

( * ) Notice: Subject to any disclaimer, the term of this patent is extended or adjusted under 35 U.S.C. 154(b) by 423 days.

(21) Appl. No.: 12/529,502

(22) PCT Filed: Feb. 28, 2008

(86) PCT No.: PCT/EP2008/052417
§ 371 (c)(1),
(2), (4) Date: Sep. 1, 2009

(87) PCT Pub. No.: WO2008/104584
PCT Pub. Date: Sep. 4, 2008

(65) Prior Publication Data
US 2010/0056561 A1 Mar. 4, 2010

(30) Foreign Application Priority Data
Mar. 1, 2007 (GB) .................................. 0703998.5

(51) Int. Cl.
*A61K 31/46* (2006.01)
*C07D 451/02* (2006.01)
*A61P 25/00* (2006.01)

(52) U.S. Cl. ...................................... 514/299; 546/112
(58) Field of Classification Search .................. 514/299; 546/112
See application file for complete search history.

(56) References Cited

U.S. PATENT DOCUMENTS 6,288,079 B1 * 9/2001 Scheel-Kruger et al. ...... 514/304

FOREIGN PATENT DOCUMENTS

| EP | 1779851 A | 5/2007 |
| WO | WO 97/30997 A | 8/1997 |
| WO | WO 02/11694 A2 | 2/2002 |
| WO | 02102801 | * 12/2002 |
| WO | 03045388 | * 6/2003 |
| WO | 03101453 | * 12/2003 |
| WO | WO 2005/011694 A | 2/2005 |
| WO | WO 2005/123869 A2 | 12/2005 |
| WO | 2007051594 | * 5/2007 |

OTHER PUBLICATIONS

Vaughan et al., The Journal of pharmacology and experimental therapeutics, (Jul. 2004) vol. 310, No. 1, pp. 1-7.*
Abdou, "Dissolution, Bioavailability and Bioequivalence passage," Mack Publishing Co., Easton, PA, US, Jan. 1, 1900, pp. 53-73, XP008085175.
Engel et al., "Salt form selection and characterization of LY333531 mesylate monohydrate," International Journal of Pharmaceutics, Amsterdam, vol. 198, No. 2, Apr. 5, 2000, pp. 239-247.
International Search Report dated Jun. 19, 2008 for corresponding International Application No. PCT/EP2008/052417.
Spurlock, "Increasing Solubility of Enoxacin and Norfloxacin by Means of Salt Formation," Journal of Parenteral Science and Technology, vol. 40, No. 2, Mar. 1, 1986, pp. 70-72, XP000577919.

* cited by examiner

*Primary Examiner* — Niloofar Rahmani
(74) *Attorney, Agent, or Firm* — Birch, Stewart, Kolasch & Birch, LLP

(57) ABSTRACT

The invention relates to a hydrochloride salt of (1R,2R,3S,5S)-3-(3,4-dichlorophenyl)-2-[(methyloxy)methyl]-8-azabicyclo[3.2.1]octane, uses of the salt as a medicament in the treatment inter alia of disorders of the central nervous system and pharmaceutical compositions and dosage forms comprising the salt.

14 Claims, 12 Drawing Sheets

Figure 1:
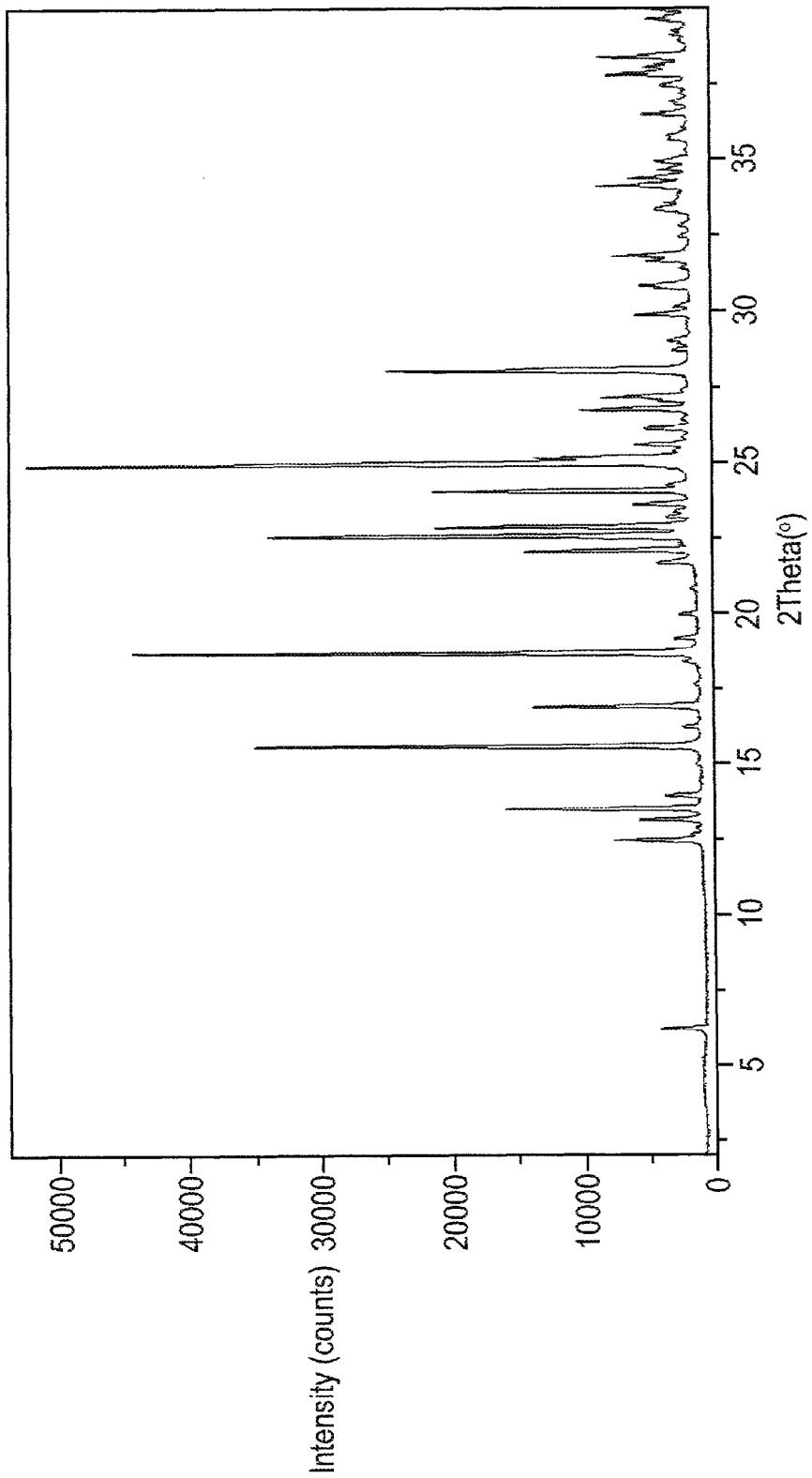

TGA data from the product of Example 1.

FTIR spectrum from the product of Example 1.

Raman spectrum from the product of Example 1.

TGA data from the product of Example 2.

FTIR spectrum from the product from Example 2.

Raman spectrum from the product of Example 2.

XRPD spectrim from the product of Example 3.

Raman spectrum from the product of Example 3.

HYDROCHLORIDE SALT OF AN AZABICYCLO[3.2.1]OCTANE DERIVATIVE

The present invention relates to a hydrochloride salt of (1R,2R,3S,5S)-3-(3,4-dichlorophenyl)-2-[(methyloxy)methyl]-8-azabicyclo[3.2.1]octane, uses of the salt as a medicament in the treatment inter alia of disorders of the central nervous system and pharmaceutical compositions and dosage forms comprising the salt.

The compound (1R,2R,3S,5S)-3-(3,4-dichlorophenyl)-2-[(methyloxy)methyl]-8-azabicyclo[3.2.1]octane of Formula (A) (i.e. the free base) and its citrate salt are described in International Patent Publication WO97/30997 (see Example 15 therein) incorporated herein by reference.

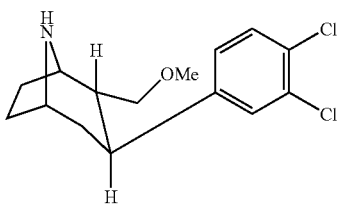

Formula (A)

The L-tartrate salt of the compound of formula (A) is described in International Patent Publication WO02/011694.

International Patent Publication WO2005/123569 (incorporated herein by reference) describes methods, apparatus, systems and machines for the preparation of drug dosage forms. The methods described in WO2005/123569 require the dissolution of the drug substance in a suitable solvent system such as methanol. However, the compound of formula (A) and prior art salts of the compound of formula (A) are insufficiently soluble and/or insufficiently stable in solvents, such as methanol, rendering them unsuitable for use in such methods.

It is an object of the invention to identify a pharmaceutically acceptable salt of the compound of formula (A) with improved solubility in appropriate solvents, such as methanol, to permit its use in such a process.

It is also an object of the invention to identify a pharmaceutically acceptable salt of the compound of formula (A) with improved stability in appropriate solvents, such as methanol, to permit its use in such a process. In this context, the word "stability" means that the compound is not susceptible to solvent-mediated conversion to other solid state forms.

In a first aspect, the invention provides a hydrochloride salt of (1R,2R,3S,5S)-2-methoxymethyl-3-(3,4-dichlorophenyl)-8-azabicyclo[3.2.1]octane.

The hydrochloride salt may be an anhydrate or a solvate (such as a hydrate). In an embodiment, the hydrochloride salt is an anhydrate. In an embodiment, the hydrochloride salt is anhydrous. In this context, the word anhydrous means the absence of water in the crystal lattice.

The hydrochloride salt may be amorphous or crystalline. In an embodiment, the hydrochloride salt is crystalline.

The hydrochloride salt of the invention, may exist in a number of polymorphic forms.

In an embodiment, the hydrochloride salt is a crystalline anhydrate with a crystal structure characterised by the following X-ray powder diffraction (XRPD) peak list:

| Position (±0.2 °2theta) | d-spacing (angstroms) |
| --- | --- |
| 6.2 | 14.2 |
| 12.5 | 7.1 |
| 13.5 | 6.6 |
| 15.6 | 5.7 |
| 18.7 | 4.8 |

In an embodiment, the hydrochloride salt is a crystalline anhydrate with a crystal structure characterised by the following XRPD peak list:

| Position (±0.1 °2theta) | d-spacing (angstroms) |
| --- | --- |
| 6.2 | 14.2 |
| 12.5 | 7.1 |
| 13.5 | 6.6 |
| 15.6 | 5.7 |
| 18.7 | 4.8 |

In an embodiment, the hydrochloride salt is a crystalline anhydrate with a crystal structure characterised by the following XRPD peak list:

| Position (±0.2 °2theta) | d-spacing (angstroms) |
| --- | --- |
| 6.2 | 14.2 |
| 12.5 | 7.1 |
| 13.1 | 6.7 |
| 13.5 | 6.6 |
| 15.6 | 5.7 |
| 16.9 | 5.2 |
| 18.7 | 4.8 |
| 21.7 | 4.1 |
| 22.0 | 4.0 |
| 22.5 | 3.9 |
| 22.8 | 3.9 |
| 24.0 | 3.7 |
| 24.9 | 3.6 |
| 25.1 | 3.5 |
| 25.6 | 3.5 |
| 26.1 | 3.4 |
| 26.7 | 3.3 |
| 27.1 | 3.3 |
| 28.0 | 3.2 |
| 29.9 | 3.0 |

In an embodiment, the hydrochloride salt is a crystalline anhydrate with a crystal structure characterised by the following XRPD peak list:

| Position (±0.1 °2theta) | d-spacing (angstroms) |
| --- | --- |
| 6.2 | 14.2 |
| 12.5 | 7.1 |
| 13.1 | 6.7 |
| 13.5 | 6.6 |
| 15.6 | 5.7 |
| 16.9 | 5.2 |
| 18.7 | 4.8 |
| 21.7 | 4.1 |
| 22.0 | 4.0 |
| 22.5 | 3.9 |
| 22.8 | 3.9 |

-continued

| Position (±0.1 °2theta) | d-spacing (angstroms) |
|---|---|
| 24.0 | 3.7 |
| 24.9 | 3.6 |
| 25.1 | 3.5 |
| 25.6 | 3.5 |
| 26.1 | 3.4 |
| 26.7 | 3.3 |
| 27.1 | 3.3 |
| 28.0 | 3.2 |
| 29.9 | 3.0 |

In an embodiment, the hydrochloride salt has a crystal structure characterised by the XRPD spectrum substantially the same as in FIG. 1.

XRPD data was determined using a PANalytical X'Pert Pro powder diffractometer, model PW3040/60, serial number DY1379 using an X'Celerator detector, the acquisition conditions being: Radiation: Cu Kα, generator tension: 40 kV; Generator current: 45 mA; Start angle: 2.0 °2theta; End angle: 40.0 °2theta; Step size: 0.0167 °2theta; and Time per step: 300 seconds. The sample was lightly ground and loaded on to a zero background plate.

In an embodiment, the hydrochloride salt has a crystal structure characterised by a melting endotherm with an onset of 211±3° C. in the DSC thermogram.

DSC thermograms were determined using a TA Instruments Q1000 calorimeter at a heating rate of 10° C. min$^{-1}$. Samples were lightly ground and added to a lightly crimped, unsealed aluminium pan (available from TA Instruments, part number: 900786.901)

In an embodiment, the hydrochloride salt has a crystal structure characterised by the following absorption peaks in the infrared spectrum of the solid product at 2858, 2767, 2715, 2581, 2503, 1472, 1411, 1368, 1272, 1191, 1137, 1125, 1090, 1058, 1028, 927, 914, 906, 879, 820, 808, 782, 706, 692 and 669±4 cm$^{-1}$.

In an embodiment, the hydrochloride salt has a crystal structure characterised by the following absorption peaks in the infrared spectrum of the solid product at 2858, 2767, 2715, 2657, 2581, 2503, 1603, 1564, 1472, 1411, 1385, 1368, 1336, 1286, 1272, 1251, 1191, 1137, 1125, 1090, 1058, 1028, 966, 951, 927, 914, 906, 879, 820, 808, 782, 739, 706, 692 and 669±4 cm$^{-1}$.

Figure 4:
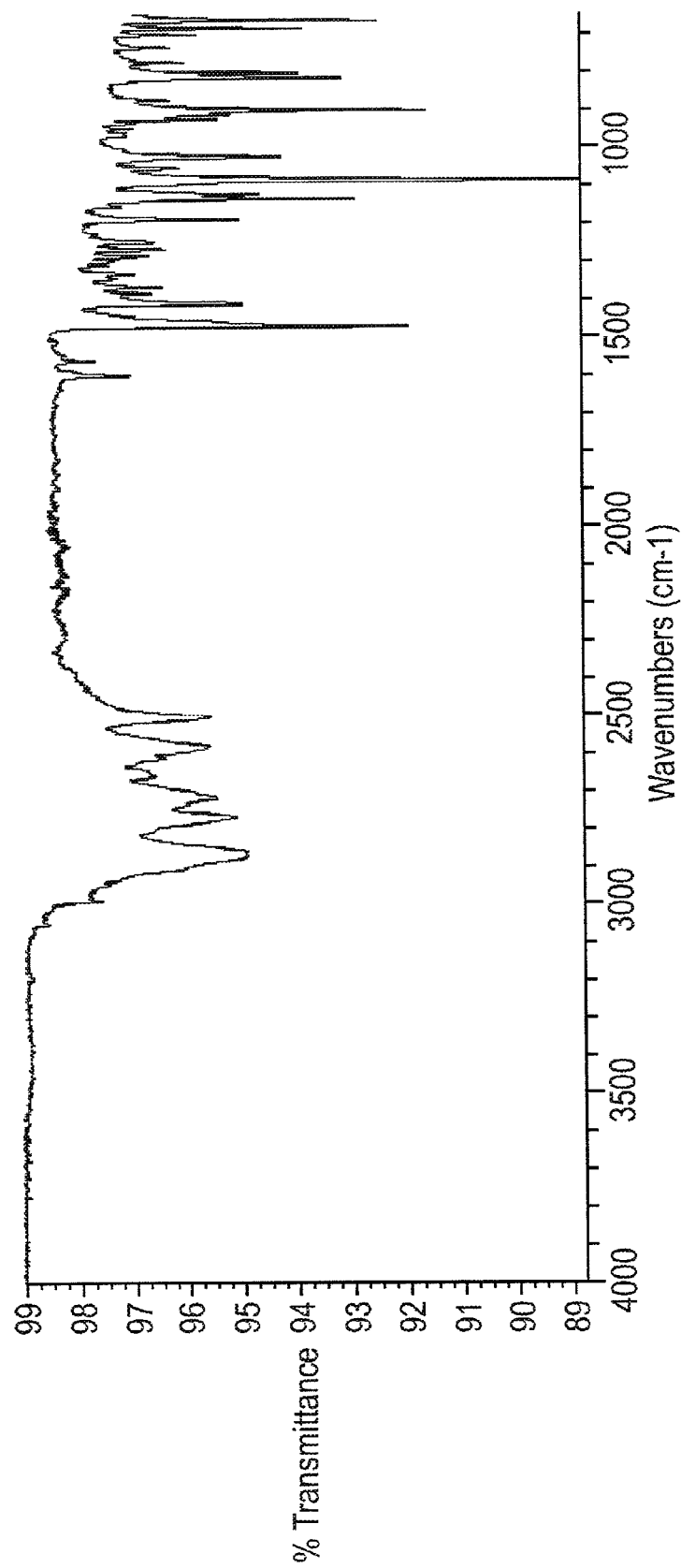

In an embodiment, the hydrochloride salt has a crystal structure characterised in that it has an infra red spectrum substantially the same as in FIG. 4.

Infrared spectra were determined using a Perkin Elmer Spectrum One FT-IR spectrometer fitted with a Diamond/ZnSe Universal ATR Accessory at 2 cm$^{-1}$ resolution. Data were digitised at 1 cm$^{-1}$ intervals.

In an embodiment, the hydrochloride salt has a crystal structure characterised by the following peaks in the Raman spectrum at 3072, 2994, 2980, 2965, 2935, 2905, 2870, 1592, 1462, 1442, 1210, 1028, 907, 880, 820, 670, 530, 486, 460, 432, 395, 318, 240, 201, 171, 143, 94 and 68±4 cm$^{-1}$.

Figure 5:
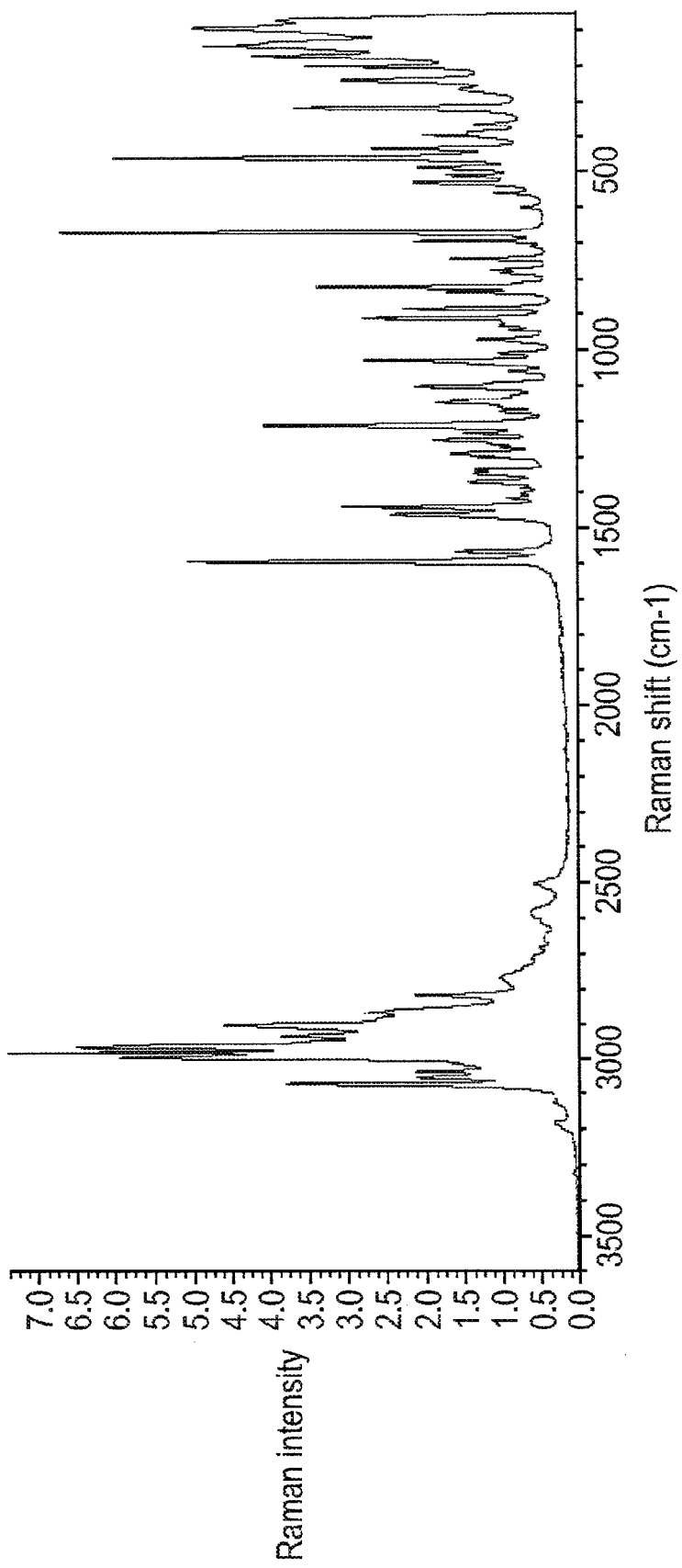

In a further embodiment, the hydrochloride salt has a crystal structure characterised in that it has a Raman spectrum substantially the same as in FIG. 5.

Raman spectra were determined using a sample in an NMR tube using a Nicolet 960 E.S.P. FT-Raman spectrometer, at 4 cm$^{-1}$ resolution with excitation from a Nd:VO4 laser (1064 nm) with a power output of 400 mW.

The hydrochloride salt as defined in the first aspect and embodiments thereof, is hereinafter referred to as the "salt of the invention".

The salt of the invention includes all suitable isotopic variations thereof. An isotopic variation is defined as one in which at least one atom is replaced by an atom having the same atomic number but an atomic mass different from the atomic mass usually found in nature. Examples of isotopes that can be incorporated include isotopes of hydrogen, carbon, nitrogen, oxygen and chlorine such as $^{2}H$, $^{3}H$, $^{13}C$, $^{14}C$, $^{15}N$, $^{17}O$, $^{18}O$ and $^{36}Cl$, respectively. Certain isotopic variations, for example, those in which a radioactive isotope such as $^{3}H$ or $^{14}C$ is incorporated, are useful in drug and/or substrate tissue distribution studies. Tritiated, i.e. $^{3}H$, and carbon-14, i.e. $^{14}C$, isotopes are suitable for their ease of preparation and detectability. Further, substitution with isotopes such as deuterium, i.e. $^{2}H$, may afford certain therapeutic advantages resulting from greater metabolic stability, for example, increased in vivo half-life or reduced dosage requirements and hence may be suitable in some circumstances. Isotopic variations can generally be prepared by conventional procedures such as by the illustrative methods or by the preparations described in the Examples and Descriptions hereafter using appropriate isotopic variations of suitable reagents.

The salt of the invention inhibits reuptake of the monoamines dopamine, noradrenaline and serotonin in synaptosomes and accordingly is useful in the treatment or prevention of diseases and conditions mediated by inhibition of the monoamines dopamine, noradrenaline and serotonin in synaptosomes.

Therefore according to a further aspect, the invention provides a salt of the invention for use as a medicament, suitably a medicament for humans.

According to a further aspect, the invention provides the use of the salt of the invention in the manufacture of a medicament for treating or preventing a disease or condition mediated by inhibition of the monoamines dopamine, noradrenaline and serotonin in synaptosomes.

In an embodiment, diseases or conditions that may be mediated by inhibition of the monoamines dopamine, noradrenaline and serotonin in synaptosomes are selected from the list consisting of: [the numbers in brackets after the listed diseases below refer to the classification code in Diagnostic and Statistical Manual of Mental Disorders, 4th Edition, published by the American Psychiatric Association (DSM-IV) and/or the International Classification of Diseases, 10th Edition (ICD-10)]:

i) Psychotic disorders for example Schizophrenia (including the subtypes Paranoid Type (295.30), Disorganised Type (295.10), Catatonic Type (295.20), Undifferentiated Type (295.90) and Residual Type (295.60)); Schizophreniform Disorder (295.40); Schizoaffective Disorder (295.70) (including the subtypes Bipolar Type and Depressive Type); Delusional Disorder (297.1) (including the subtypes Erotomanic Type, Grandiose Type, Jealous Type, Persecutory Type, Somatic Type, Mixed Type and Unspecified Type); Brief Psychotic Disorder (298.8); Shared Psychotic Disorder (297.3); Psychotic Disorder due to a General Medical Condition (including the subtypes with Delusions and with Hallucinations); Substance-Induced Psychotic Disorder (including the subtypes with Delusions (293.81) and with Hallucinations (293.82)); and Psychotic Disorder Not Otherwise Specified (298.9).

ii) Depression and mood disorders for example Depressive Episodes (including Major Depressive Episode, Manic Episode, Mixed Episode and Hypomanic Episode); Depressive Disorders (including Major Depressive Disorder, Dysthymic Disorder (300.4), Depressive Disorder Not Otherwise Specified (311)); Bipolar Disorders (including Bipolar I Disorder, Bipolar II Disorder (i.e. Recurrent Major Depressive Episodes with Hypomanic Episodes) (296.89), Cyclothymic Disorder (301.13) and Bipolar Disorder Not Otherwise Specified (296.80)); Other Mood Disorders (including Mood Disorder due to a General Medical Condition (293.83) which includes the subtypes With Depressive Features, With Major Depressive-like Episode, With Manic Features and With Mixed Features); Substance-Induced Mood Disorder (including the subtypes With Depressive Features, With Manic Features and With Mixed Features); and Mood Disorder Not Otherwise Specified (296.90).

iii) Anxiety disorders for example Social Anxiety Disorder; Panic Attack; Agoraphobia, Panic Disorder; Agoraphobia Without History of Panic Disorder (300.22); Specific Phobia (300.29) (including the subtypes Animal Type, Natural Environment Type, Blood-Injection-Injury Type, Situational Type and Other Type); Social Phobia (300.23); Obsessive-Compulsive Disorder (300.3); Posttraumatic Stress Disorder (309.81); Acute Stress Disorder (308.3); Generalized Anxiety Disorder (300.02); Anxiety Disorder Due to a General Medical Condition (293.84); Substance-Induced Anxiety Disorder; and Anxiety Disorder Not Otherwise Specified (300.00).

iv) Substance-related disorders for example Substance Use Disorders (including Substance Dependence, Substance Craving and Substance Abuse); Substance-Induced Disorders (including Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders (including Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9)); Amphetamine (or Amphetamine-Like)-Related Disorders (for example Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9)); Caffeine Related Disorders (including Caffeine Intoxication (305.90), Caffeine-Induced Anxiety Disorder, Caffeine-Induced Sleep Disorder and Caffeine-Related Disorder Not Otherwise Specified (292.9)); Cannabis-Related Disorders (including Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9)); Cocaine-Related Disorders (including Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9)); Hallucinogen-Related Disorders (including Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9)); Inhalant-Related Disorders (including Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9)); Nicotine-Related Disorders (including Nicotine Dependence (305.1), Nicotine Withdrawal (292.0) and Nicotine-Related Disorder Not Otherwise Specified (292.9)); Opioid-Related Disorders (including Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9)); Phencyclidine (or Phencyclidine-Like)-Related Disorders (including Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9)); Sedative-, Hypnotic-, or Anxiolytic-Related Disorders (including Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9)); Polysubstance-Related Disorder (including Polysubstance Dependence (304.80)); and Other (or Unknown) Substance-Related Disorders (including Anabolic Steroids, Nitrate Inhalants and Nitrous Oxide).

v) Sleep disorders for example primary sleep disorders such as Dyssomnias (including Primary Insomnia (307.42), Primary Hypersomnia (307.44), Narcolepsy (347), Breathing-Related Sleep Disorders (780.59), Circadian Rhythm Sleep Disorder (307.45) and Dyssomnia Not Otherwise Specified (307.47)); primary sleep disorders such as Parasomnias (including Nightmare Disorder (307.47), Sleep Terror Disorder (307.46), Sleepwalking Disorder (307.46) and Parasomnia Not Otherwise Specified (307.47)); Sleep Disorders Related to Another Mental Disorder (including Insomnia Related to Another Mental Disorder (307.42)

and Hypersomnia Related to Another Mental Disorder (307.44)); Sleep Disorder Due to a General Medical Condition; and Substance-Induced Sleep Disorder (including the subtypes Insomnia Type, Hypersomnia Type, Parasomnia Type and Mixed Type).

vi) Eating disorders such as Anorexia Nervosa (307.1) (including the subtypes Restricting Type and Binge-Eating/Purging Type); Bulimia Nervosa (307.51) (including the subtypes Purging Type and Nonpurging Type); Obesity; Compulsive Eating Disorder; Binge Eating Disorder; and Eating Disorder Not Otherwise Specified (307.50).

vii) Autism Spectrum Disorders including Autistic Disorder (299.00), Asperger's Disorder, Rett's Disorder, Childhood Disintegrative Disorder and Pervasive Developmental Disorder Not Otherwise Specified.

viii) Attention-Deficit/Hyperactivity Disorder (including the subtypes Attention-Deficit/Hyperactivity Disorder Combined Type (314.01), Attention-Deficit/Hyperactivity Disorder Predominantly Inattentive Type (314.00), Attention-Deficit/Hyperactivity Disorder Hyperactive-Impulse Type (314.01) and Attention-Deficit/Hyperactivity Disorder Not Otherwise Specified (314.9)); Hyperkinetic Disorder; Disruptive Behaviour Disorders such as Conduct Disorder (including the subtypes childhood-onset type (321.81), Adolescent-Onset Type (312.82) and Unspecified Onset (312.89), Oppositional Defiant Disorder (313.81) and Disruptive Behaviour Disorder Not Otherwise Specified; and Tic Disorders such as Tourette's Disorder (307.23).

ix) Personality Disorders including the subtypes Paranoid Personality Disorder (301.0), Schizoid Personality Disorder (301.20), Schizotypal Personality Disorder (301,22), Antisocial Personality Disorder (301.7), Borderline Personality Disorder (301,83), Histrionic Personality Disorder (301.50), Narcissistic Personality Disorder (301,81), Avoidant Personality Disorder (301.82), Dependent Personality Disorder (301.6), Obsessive-Compulsive Personality Disorder (301.4) and Personality Disorder Not Otherwise Specified (301.9).

x) Enhancement of cognition including the treatment of cognition impairment in other diseases such as schizophrenia, bipolar disorder, depression, other psychiatric disorders and psychotic conditions associated with cognitive impairment, e.g. Alzheimer's disease.

xi) Sexual dysfunctions such as Sexual Desire Disorders (including Hypoactive Sexual Desire Disorder (302.71) and Sexual Aversion Disorder (302.79)); sexual arousal disorders (including Female Sexual Arousal Disorder (302.72) and Male Erectile Disorder (302.72)); orgasmic disorders (including Female Orgasmic Disorder (302.73), Male Orgasmic Disorder (302.74) and Premature Ejaculation (302.75)).

In an embodiment, diseases or conditions that may be mediated by inhibition of the monoamines dopamine, noradrenaline and serotonin in synaptosomes are selected from the group i) Psychotic disorders, ii) Depression and mood disorders, iii) Anxiety disorders and xi) Sexual dysfunctions.

In an embodiment, diseases or conditions that may be mediated by inhibition of the monoamines dopamine, noradrenaline and serotonin in synaptosomes are ii) Depression and mood disorders or iii) Anxiety disorders.

In an embodiment, when the disease or condition that may be mediated by inhibition of the monoamines dopamine, noradrenaline and serotonin in synaptosomes disease is xi) Sexual Dysfunction, the disease or condition is Premature Ejaculation (302.75).

It will be appreciated that references herein to "treatment" extend to prophylaxis, prevention of recurrence and suppression or amelioration of symptoms (whether mild, moderate or severe) as well as the treatment of established conditions.

The salt of the invention may be used in combination with the following agents to treat or prevent psychotic disorders: i) antipsychotics; ii) drugs for extrapyramidal side effects, for example anticholinergics (such as benztropine, biperiden, procyclidine and trihexyphenidyl), antihistamines (such as diphenhydramine) and dopaminergics (such as amantadine); iii) antidepressants; iv) anxiolytics; and v) cognitive enhancers for example cholinesterase inhibitors (such as tacrine, donepezil, rivastigmine and galantamine).

The salt of the invention may be used in combination with antidepressants to treat or prevent depression and mood disorders.

The salt of the invention may be used in combination with the following agents to treat or prevent bipolar disease: i) mood stabilisers; ii) antipsychotics; or iii) antidepressants.

The salt of the invention may be used in combination with the following agents to treat or prevent anxiety disorders: i) anxiolytics; or ii) antidepressants.

The salt of the invention may be used in combination with the following agents to treat or prevent male sexual dysfunction: i) phosphodiesterase V inhibitors, for example vardenafil and sildenafil; ii) dopamine agonists/dopamine transport inhibitors for example apomorphine and buprorion; iii) alpha adrenoceptor antagonists for example phentolamine; iv) prostaglandin agonists for example alprostadil; v) testosterone agonists such as testosterone; vi) serotonin transport inhibitors for example serotonin reuptake inhibitors; vii) noradrenaline transport inhibitors for example reboxetine and viii) 5-HT$_{1A}$ agonists, for example flibanserine.

The salt of the invention may be used in combination with the same agents specified for male sexual dysfunction to treat or prevent female sexual dysfunction, and in addition an estrogen agonist such as estradiol.

Antipsychotic drugs include typical antipsychotics (for example chlorpromazine, thioridazine, mesoridazine, fluphenazine, perphenazine, prochlorperazine, trifluoperazine, thiothixine, haloperidol, molindone and loxapine); and atypical antipsychotics (for example clozapine, olanzapine, risperidone, quetiapine, aripirazole, ziprasidone and amisulpride).

Antidepressant drugs include serotonin reuptake inhibitors (such as citalopram, escitalopram, fluoxetine, paroxetine, sertraline femoxetine, fluvoxamine, indalpine and zimeldine); dual serotonin/noradrenaline reuptake inhibitors (such as venlafaxine, duloxetine and milnacipran); noradrenaline reuptake inhibitors (such as reboxetine and venlafaxine); tricyclic antidepressants (such as amitriptyline, clomipramine, imipramine, maprotiline, nortriptyline and trimipramine); monoamine oxidase inhibitors (such as isocarboxazide, moclobemide, phenelzine and tranylcypromine); and others (such as bupropion, mianserin, mirtazapine, nefazodone and trazodone).

Mood stabiliser drugs include lithium, sodium valproate/valproic acid/divalproex, carbamazepine, lamotrigine, gabapentin, topiramate and tiagabine.

Anxiolytics include benzodiazepines such as alprazolam and lorazepam.

In addition the salt of the invention may be administered in combination with 5-HT$_3$ antagonists (such as ondansetron, granisetron and metoclopramide); serotonin agonists (such as sumatriptan, rauwolscine, yohimbine and metoclopramide); and/or NK-1 antagonists.

It will be appreciated that the abovementioned combinations may be administered simultaneously (either in the same or different pharmaceutical formulations), separately or sequentially.

The salt of the invention may be administered alone, but it will generally be administered as a formulation in conjunction with one or more pharmaceutically acceptable excipients, selected with regard to the intended route of administration and standard pharmaceutical practice. Therefore according to a further aspect, the invention provides a pharmaceutical composition comprising a salt of the invention, in association with one or more pharmaceutically acceptable excipients. The excipient must be "acceptable" in the sense of being compatible with the other ingredients of the composition and not deleterious to the recipient thereof.

As described hereinabove, the preparation of a suitable dosage form of the salt of the invention involves methods, apparatus, systems and machines described in International Patent Publication WO2005/123569 (incorporated herein by reference). WO2005/123569 describes a method for producing a pharmaceutical product comprising the steps of: a) addition of a metered liquid dose onto each of a plurality of carrier substrates, the liquid dose containing the active agent dissolved in a suitable solvent system; b) evaporation of the solvent in for example an oven so as to capture the active agent in or on the carrier substrate; and c) optionally, providing a coating over the active agent.

Therefore according to a further aspect the invention provides a method for making a dosage form of the salt of the invention, the method comprising: a) addition of a metered liquid dose onto each of a plurality of carrier substrates; the liquid dose comprising the salt of the invention dissolved in a suitable solvent system; b) evaporation of the solvent; and c) optionally providing a coating over the salt of the invention.

According to a further aspect, the invention provides the method as defined in any one of claims 59 to 64 of WO2005/123569, wherein the active agent is the salt of the invention.

According to a further aspect, the invention provides a pharmaceutical dosage form obtainable by such a method.

According to a further aspect, the invention provides the salt of the invention dissolved in a solvent system.

According to a further aspect, the invention provides a liquid dose comprising a salt of the invention dissolved in a solvent system.

In an embodiment, the solvent system is selected so as to solubilise the salt of the invention. In a further embodiment, the solvent system is methanol, aqueous methanol, ethanol, aqueous ethanol, water, methylene chloride, acetone or acetic acid, or a mixture thereof. In a yet further embodiment, the solvent system is methanol.

In an embodiment, the solvent system includes one or more polymers which are soluble in the solvent system. These polymers enhance adhesion of the liquid dose and the salt of the invention to the carrier substrate. In an embodiment, the polymer is selected from hydroxypropyl cellulose, hydroxypropylmethyl cellulose, hydroxyethyl cellulose, carboxymethyl cellulose, polyvinyl alcohol, polyvinylpyrrolidone, carrageenan, gelatine, polyethylene glycol, polyethylene oxide, pullulan and acrylic copolymer, or a combination thereof. In an embodiment, the polymer is hydroxypropyl cellulose. We have found that certain solvent systems, such as those comprising water, require addition of surfactants and/or anti-foaming agents. Therefore in a further embodiment, the solvent system includes one or more surfactants (such as sorbitan trioleate, sorbitan tristearate, glyceryl monostearate and polysorbate 80) and/or one or more anti-foaming agents.

In an embodiment, the liquid dose delivered to each carrier substrate is from 5 to 10 microliters. In a further embodiment the liquid dose comprises a) from 11.6 to 35.0% (w/w) salt of the invention and b) from 4 to 15% (w/v) of hydroxypropylcellulose in methanol with a variety of molecular weights of hydroxypropylcellulose.

According to a further aspect, the invention provides a pharmaceutical dosage form comprising a carrier substrate and the salt of the invention.

The carrier substrate onto which the liquid dose is added may comprise a film-coat. The film-coat is selected with regard to the chosen solvent system. For non-aqueous solvent systems, an aqueous film-coat such as Opadry may be used. For aqueous solvent systems, aqueous based film-coats may cause disintegration of the carrier substrate, therefore non-aqueous film-coats such as ethylcellulose (eg Surelease) or methacrylate (eg Eudragit) should be used. The film-coat is applied to the carrier substrate to achieve a weight gain of between 2-10%. In an embodiment, the film-coat is Opadry and is applied to the carrier substrate to a weight gain of 4%. The composition of the carrier substrate and the presence of a film-coat will determine the extent to which the liquid dose and hence the salt of the invention wicks into the carrier substrate.

In an embodiment, the salt of the invention is substantially on the surface of the carrier substrate.

In a further embodiment, there is provided a coating over the salt of the invention.

The carrier substrate may be formed using conventional tabletting technology well known to the skilled person. For example a compression tablet may comprise diluent, binder and lubricant. Other suitable excipients are well known to the skilled formulation chemist (see Pharmaceutical Dosage Forms: Tablets, Vol. 2 (Pharmaceutical Dosage Forms-Tablets), 1989 by Herbert Lieberman (Editor), Leon Lachman (Editor), Joseph B. Schwartz (Editor). Alternatively, carrier substrates may be formed by injection moulding. Suitable thermoplastic materials for injection moulding include hydroxpropyl cellulose, ethylcellulose, methyacrylates and polyvinyl acetate.

In an embodiment, the carrier substrate is a tablet formed by conventional compression technology and comprises diluent, binder and lubricant. In an embodiment, the diluent is from 0-100% w/w, the binder is 0-100% w/w and the lubricant is 0-25% w/w. In an embodiment the diluent is microcrystalline cellulose (such as Avicel PH-102), the binder is pregelatinised starch (Starch 1500) and the lubricant is magnesium stearate. In an embodiment, the carrier substrate has the following composition:

| Excipient | w/w |
| --- | --- |
| Microcrystalline Cellulose (such as Avicel PH-102) | 90% |
| Pregelatinised Starch (Starch 1500) | 9% |
| Magnesium Stearate | 1% |

In an alternative embodiment, the carrier substrate may be formulated such that it disintegrates in the mouth when administered orally, a so called "orally disintegrating tablet" or "ODT" substrate. Alternatively, the carrier substrate may be formulated so as to disintegrate in water, a so called "fast-dissolve tablet" or "FDT" substrate.

The carrier substrate may be shaped to provide one or more concave features on its surface, to receive the liquid dose. In an embodiment, there are two concave features, one on each side of the tablet.

The carrier substrate may carry in addition to the salt of the invention, a further one or more pharmaceutically active compounds. There are various ways this may be achieved. For example, the liquid dose may contain a mixture of the salt of the invention and one or more other pharmaceutically active compounds. Alternatively, the method could be adapted to apply one or more liquid doses each containing a single pharmaceutically active compound to each carrier substrate. Should the pharmaceutically active compounds be incompatible with each other, then the method could be adapted so as to apply the liquid dose to different parts of the tablet, for example to different sides. Alternatively, a tablet containing one or more pharmaceutically active compounds may form the carrier substrate, in the method for making the dosage form.

The coating over the salt of the invention may be applied by spraying an aqueous coating material for example Opadry™ or by applying Opadry™ by a pad-printing process. In addition, a commercial logo may be applied using an edible ink such as Opacoat™.

An alternative dosage form suitable for use with the hydrochloride salt according to the first aspect is described in International Patent publication WO97/04750 (incorporated herein by reference).

In one embodiment, the dosage form contains from 1 microgramme to 3 milligrammes of the salt of the invention. In a further embodiment, the dosage form contains from 1 microgramme to 2 milligrammes of the salt of the invention. In a further embodiment, the dosage form contains from 100 microgramme to 2 milligrammes of the salt of the invention. In a further embodiment, the dosage form contains from 500 microgrammes to 2 milligrammes of the salt of the invention.

It will be recognised by one of skill in the art that the optimal quantity and spacing of individual dosages of the salt of the invention will be determined by the nature and extent of the condition being treated, and that such optimums can be determined by conventional techniques. It will also be appreciated by one of skill in the art that the optimal course of treatment, i.e., the number of doses of the salt of the invention given per day for a defined number of days, can be ascertained by those skilled in the art using conventional courses of treatment determination tests.

All publications, including, but not limited to, patents and patent applications cited in this specification, are herein incorporated by reference as if each individual publication were specifically and individually indicated to be incorporated by reference herein as though fully set forth.

It will be appreciated that the invention includes the following further aspects. The embodiments described for the first aspect extend these further aspects. The diseases and conditions described above extend, where appropriate, to these further aspects.

i) A salt of the invention for use in treating or preventing a disease or condition mediated by inhibition of the monoamines dopamine, noradrenaline and serotonin in synaptosomes.

ii) A method of treatment or prevention of a disease or condition mediated by inhibition of the monoamines dopamine, noradrenaline and serotonin in synaptosomes in a mammal comprising administering an effective amount of a salt of the invention.

The invention is illustrated, by way of example only, by the following Examples.

Compounds are named using ACD/Name PRO6.02 chemical naming software (Advanced Chemistry Development Inc., Toronto, Ontario, M5H2L3, Canada).

EXAMPLE 1

Preparation of the Crystalline Hydrochloride Salt of (1R,2R,3S,5S)-3-(3,4-dichlorophenyl)-2-[(methyloxy)methyl]-8-azabicyclo[3.2.1]octane from the Corresponding Tartrate Salt a) Preparation of (1R,2R,5S)-3-(3,4-dichlorophenyl)-2-[(methyloxy)methyl]-8-azabicyclo[3.2.1]octane (Free Base)

A 1 liter vessel was purged with nitrogen and charged with the tartrate salt of (1R,2R,5S)-3-(3,4-dichlorophenyl)-2-[(methyloxy)methyl]-8-azabicyclo[3.2.1]octane (this salt may be prepared in accordance with the procedure described in International Patent Publication WO 2005/011694) (90 g) followed by ethyl acetate (450 ml) and aqueous potassium carbonate solution (448 ml). The mixture was stirred at room temperature for 15 minutes. The layers were separated. Demineralised water (450 ml) was added to the organic layer and stirred for 10 minutes. The layers were separated. Further demineralised water was added to the organic phase and the mixture stirred for 10 minutes. The layers were separated and the organic phase was dried using anhydrous magnesium sulphate (approx 50 g). The mixture was filtered to remove the magnesium sulphate, washing through with a small amount of ethyl acetate. The filtrate was then concentrated to half volume in vacuo using a rotary evaporator.

b) Preparation of the Hydrochloride Salt of (1R,2R,5S)-3-(3,4-dichlorophenyl)-2-[(methyloxy)methyl]-8-azabicyclo[3.2.1]octane Step a) was repeated a further two times to give three ethyl acetate solutions of the free base. These three solutions were combined and charged into a reaction vessel. Hydrogen chloride/isopropanol solution (95.34 ml of 6.047 M) was added and the solution was stirred overnight at 20 degC. The mixture was filtered and the filtercake was washed with ethyl acetate (270 ml). The solid was dried in a vacuum oven at 40 degC. to constant weight (145.26 g).

c) Recrystallisation

The product from step b) (140.68 g) was charged into a reaction vessel followed by isopropanol (422 ml). The mixture was heated under reflux. Further isopropanol was added (280 ml) to dissolve the solids. The mixture was hot vacuum filtered, and the filtrate was re-heated to dissolve any solids that had formed. The mixture was cooled at a rate of 5 degC. per hour down to 12 degC. The mixture was stirred for 2 hours. The slurry was filtered and the filter cake washed with isopropanol (140 ml). The filter cake was dried at 42 degC. in a vacuum oven to constant weight (77.81 g).

The product from Example 1 was characterised as follows.

The X-ray powder diffraction (XRPD) pattern of the product from Example 1 is shown in FIG. 1 and was characterised using a PANalytical X'Pert Pro powder diffractometer, model PW3040/60, serial number DY1379 using an X'Celerator detector. The acquisition conditions were:
  Radiation: Cu Kα, generator tension: 40 kV,
  Generator current: 45 mA,
  Start angle: 2.0 °2theta,
  End angle: 40.0 °2theta,
  Step size: 0.0167 °2theta,
  Time per step: 300 seconds.

The sample was lightly ground and loaded on to a zero background plate. Characteristic XRPD angles and d-spacings are as follows:

| Position °2Theta | d-spacing (angstroms) |
|---|---|
| 6.2 | 14.2 |
| 12.5 | 7.1 |
| 13.1 | 6.7 |
| 13.5 | 6.6 |
| 15.6 | 5.7 |
| 16.9 | 5.2 |
| 18.7 | 4.8 |
| 21.7 | 4.1 |
| 22.0 | 4.0 |
| 22.5 | 3.9 |
| 22.8 | 3.9 |
| 24.0 | 3.7 |
| 24.9 | 3.6 |
| 25.1 | 3.5 |
| 25.6 | 3.5 |
| 26.1 | 3.4 |
| 26.7 | 3.3 |
| 27.1 | 3.3 |
| 28.0 | 3.2 |
| 29.9 | 3.0 |

Figure 2:
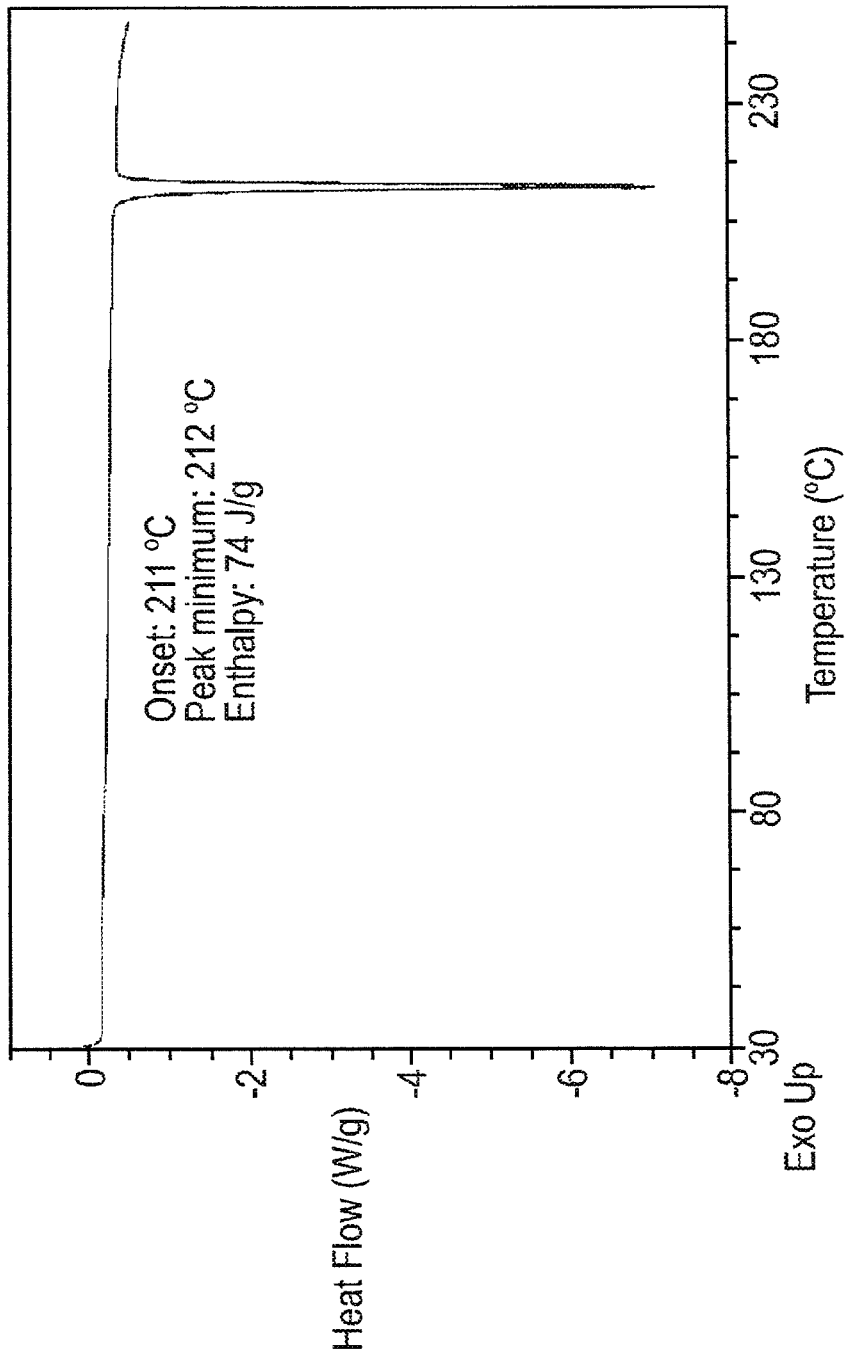

The DSC thermogram of the product from Example 1 (see FIG. 2) was obtained using a TA Instruments Q1000 calorimeter. The sample was weighed into an aluminium pan (available from TA Instruments, part number: 900786.901), a pan lid placed on top and lightly crimped without sealing the pan. The experiment was conducted using a heating rate of 10° C. min$^{-1}$. A sharp endotherm was observed at an onset temperature of 211° C.

Figure 3:
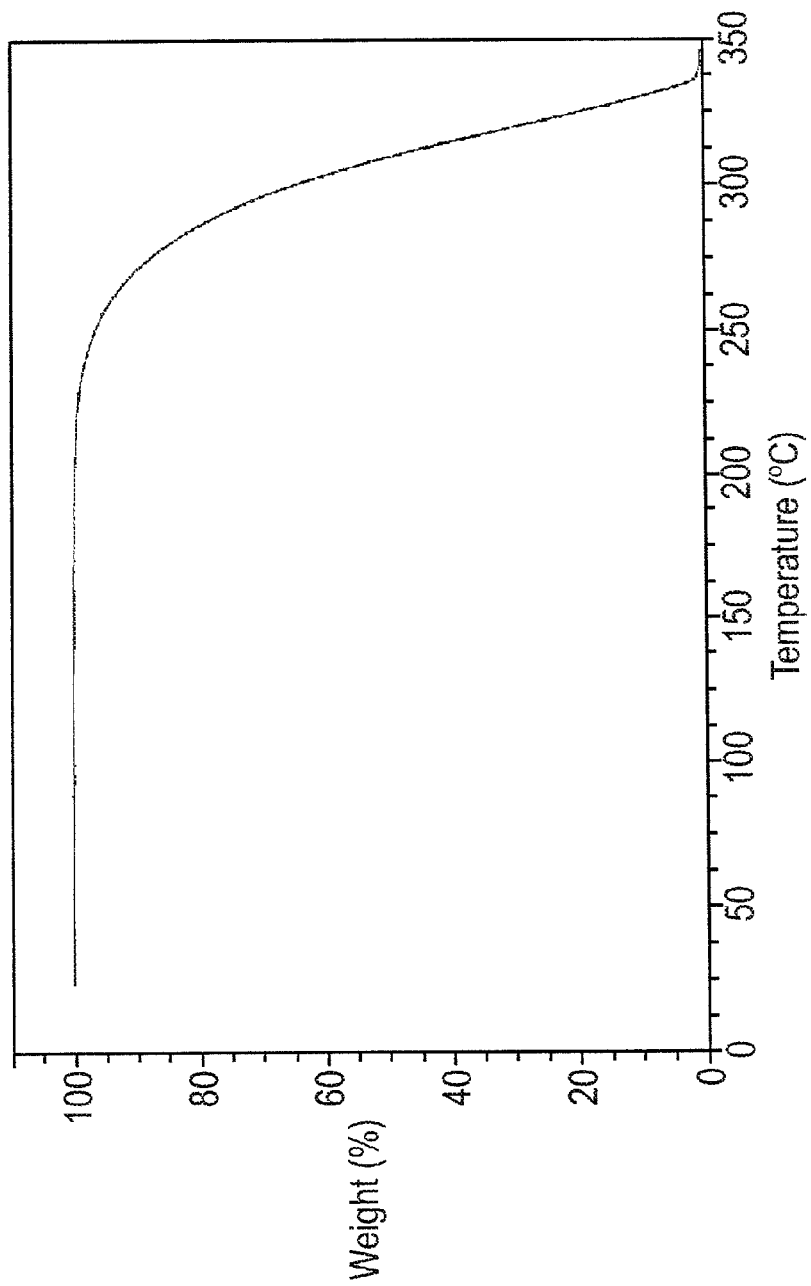

TGA of the product from Example 1 (see FIG. 3) was obtained using a TA Instruments Q500 balance and a heating rate of 10° C. min$^{-1}$. No significant weight losses are observed before thermal decomposition of the sample.

The infrared spectrum of the solid product from Example 1 (see FIG. 4) was recorded using a Perkin Elmer Spectrum One FT-IR spectrometer fitted with a Diamond/ZnSe Universal ATR Accessory at 2 cm$^{-1}$ resolution. Data were digitised at 1 cm$^{-1}$ intervals. Bands were observed at: 2858, 2767, 2715, 2657, 2581, 2503, 1603, 1564, 1472, 1411, 1385, 1368, 1336, 1286, 1272, 1251, 1191, 1137, 1125, 1090, 1058, 1028, 966, 951, 927, 914, 906, 879, 820, 808, 782, 739, 706, 692 and 669 cm$^{-1}$.

The Raman spectrum of the product from Example 1 (see FIG. 5) was recorded with the solid sample in an NMR tube using a Nicolet 960 E.S.P. FT-Raman spectrometer, at 4 cm$^{-1}$ resolution with excitation from a Nd:VO4 laser (1064 nm) with a power output of 400 mW. Bands were observed at: 3072, 2994, 2980, 2965, 2935, 2905, 2870, 1592, 1564, 1462, 1442, 1210, 1028, 907, 880, 820, 670, 530, 486, 460, 432, 395, 318, 240, 201, 171, 143, 94 and 68 cm$^{-1}$.

EXAMPLE 2

Preparation of the Crystalline Hydrochloride Salt of (1R,2R,5S)-3-(3,4-dichlorophenyl)-2-[(methyloxy) methyl]-8-azabicyclo[3.2.1]octane from (1R,2R,5S)-3-(3,4-dichlorophenyl)-8-methyl-2-[(methyloxy) methyl]-8-azabicyclo[3.2.1]octane (1R,2R,5S)-3-(3,4-Dichlorophenyl)-8-methyl-2-[(methyloxy)methyl]-8-azabicyclo[3.2.1]octane (this compound may be prepared in accordance with the procedure described in Example 11 of International Patent Publication WO 97/30997) (10.43 g) was dissolved in a mixture of toluene (21 ml) and acetone (31 ml). Hunigs base (5.83 ml) was added and the reaction mixture was heated to 50 degC. 1-Chloroethylchloroformate (7.2 ml) was added over a period of 30 minutes and stirring continued at 50 degC. for 1.5 hours. Water (8 ml) was added and heating at 50 degC. and stirring was continued for 2.5 hours. The mixture was evaporated to low volume and the water was removed by azeotroping with toluene. Toluene was added (to adjust to 50 ml) and aqueous potassium carbonate solution (100 ml containing 1.2 g of potassium carbonate). The layers were separated and the organic layer was washed with brine (2×100 ml). The layers were separated and the organic layer was evaporated to low volume. Residual water was removed by azeotropic distillation with toluene and additional toluene (20 ml) added to provide a total volume of 30 ml.

To half of this solution (15 ml) was added hydrogen chloride in isopropanol (3 ml of 5.6 M solution), then isohexane (25 ml; 5 volumes) was added and the mixture left to crystallise. The mixture was stirred for 30 minutes at room temperature, filtered and washed with isohexane. The solid was dried at 40 degC. in vacuo to give a white solid (4.30 g). The solid was recrystallised by dissolving in isopropanol (13 ml) at room temperature, followed by cooling to 15 degC. in an ice bath for 1 hour. The solid was filtered and dried at 45 degC. in vacuo to give the title product (3.4 g).

The product from Example 2 was characterised under analogous conditions to the product from Example 1.

Figure 6:
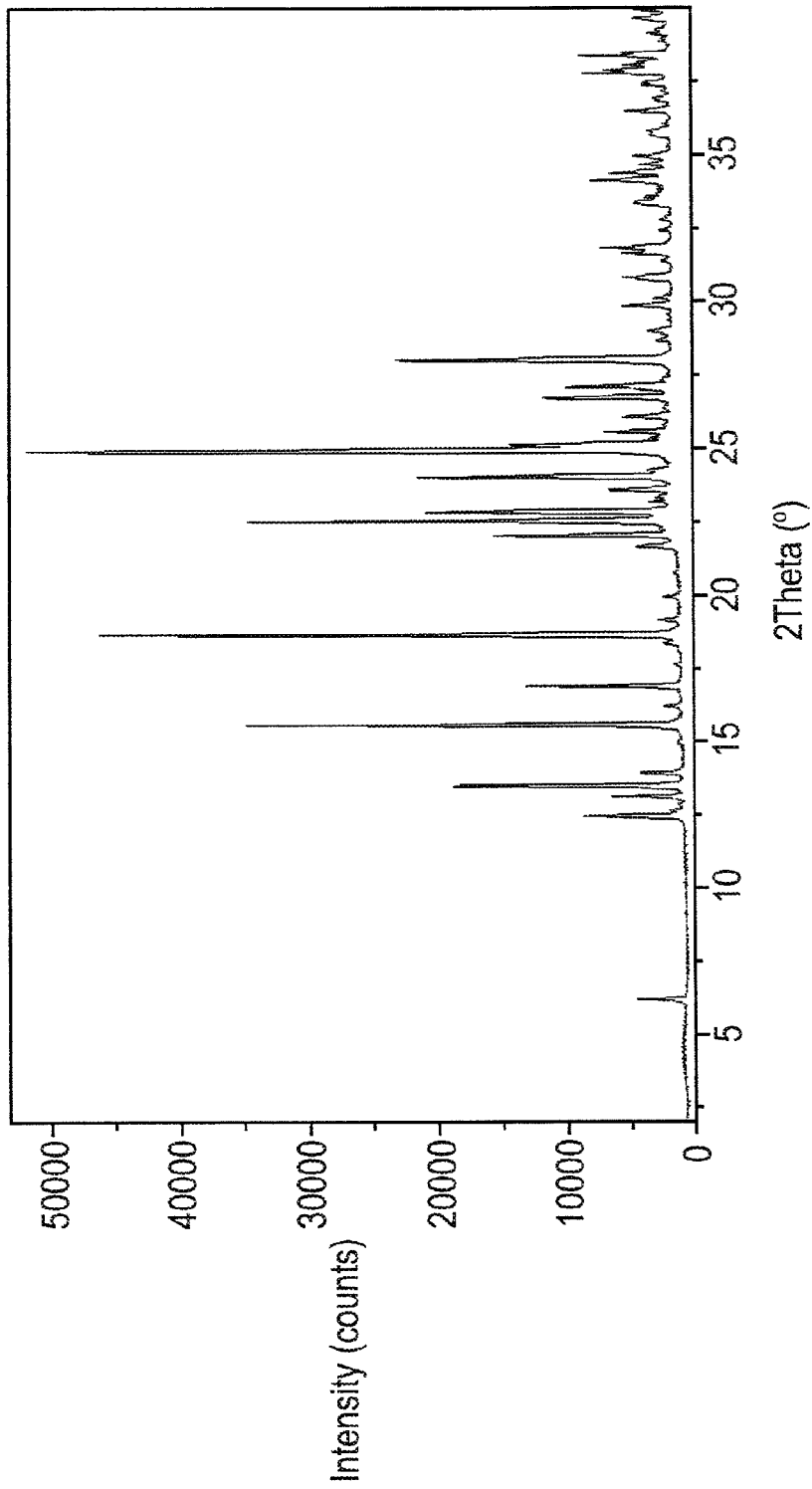

The X-ray powder diffraction (XRPD) pattern of the product is shown in FIG. 6. Characteristic XRPD angles and d-spacings are as follows:

| Position °2Theta | d-spacing (angstroms) |
|---|---|
| 6.2 | 14.2 |
| 12.5 | 7.1 |
| 13.1 | 6.7 |
| 13.5 | 6.6 |
| 15.6 | 5.7 |
| 16.9 | 5.2 |
| 18.7 | 4.8 |
| 21.7 | 4.1 |
| 22.0 | 4.0 |
| 22.5 | 3.9 |
| 22.8 | 3.9 |
| 24.0 | 3.7 |
| 24.9 | 3.6 |
| 25.1 | 3.5 |
| 25.6 | 3.5 |
| 26.1 | 3.4 |
| 26.7 | 3.3 |
| 27.1 | 3.3 |
| 28.0 | 3.2 |
| 30.0 | 3.0 |

Figure 7:
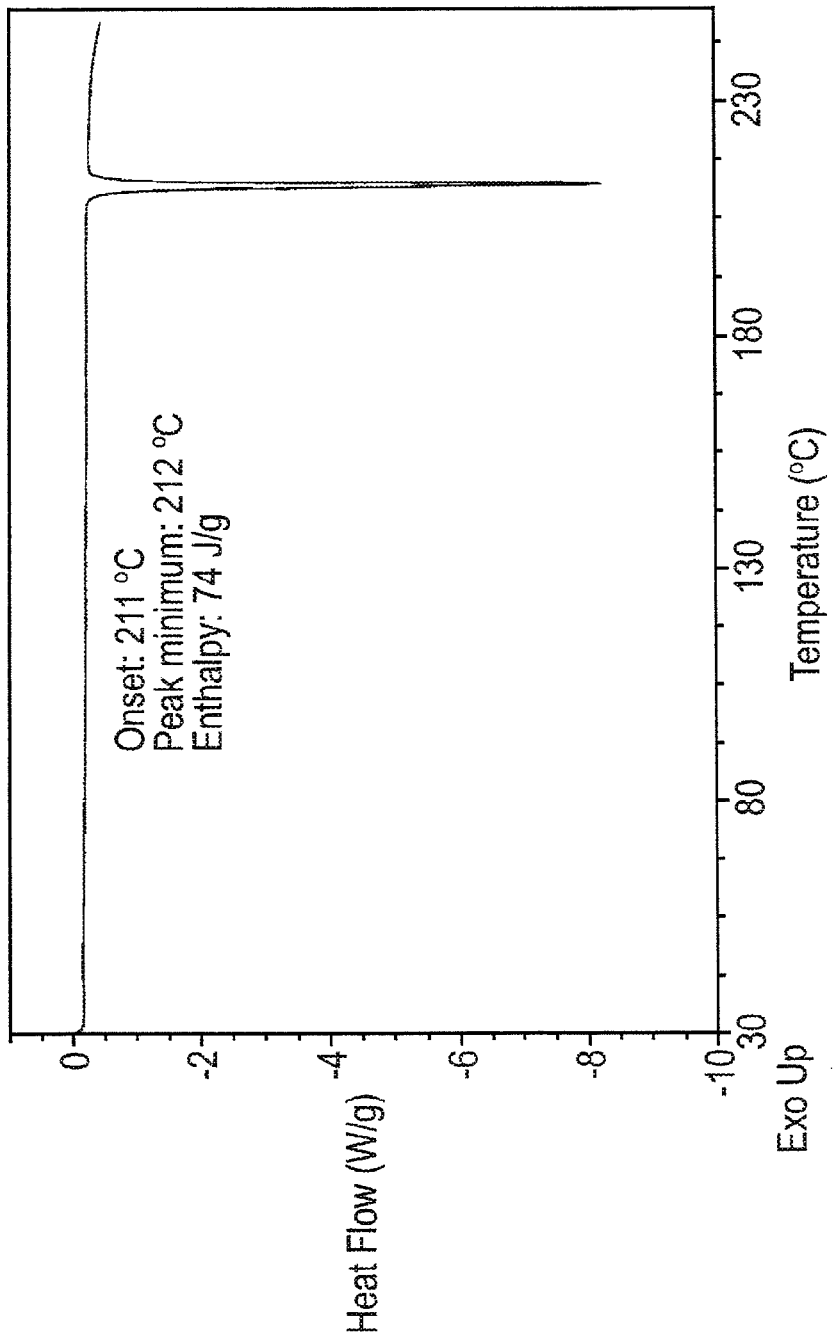

The DSC thermogram of the product from Example 2 (see FIG. 7) was obtained using a TA Instruments Q1000 calorimeter. The sample was weighed into an aluminium pan, a pan lid placed on top and lightly crimped without sealing the pan. The experiment was conducted using a heating rate of 10° C. min$^{-1}$. A sharp endotherm was observed at an onset temperature of 211° C.

Figure 8:
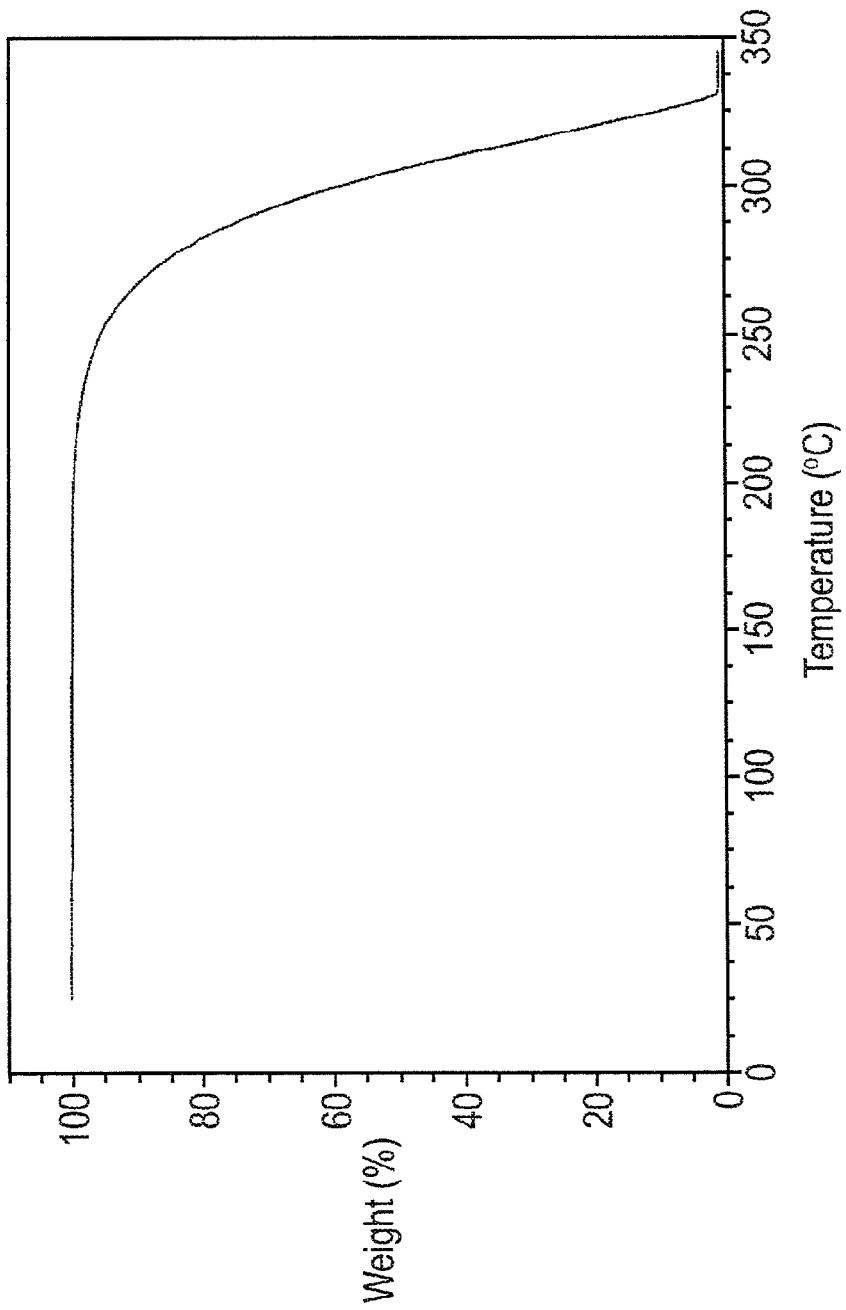

TGA of the product from Example 2 (see FIG. 8) was obtained using a TA Instruments Q500 balance and a heating rate of 10° C. min$^{-1}$. No significant weight losses were observed before thermal decomposition of the sample.

Figure 9:
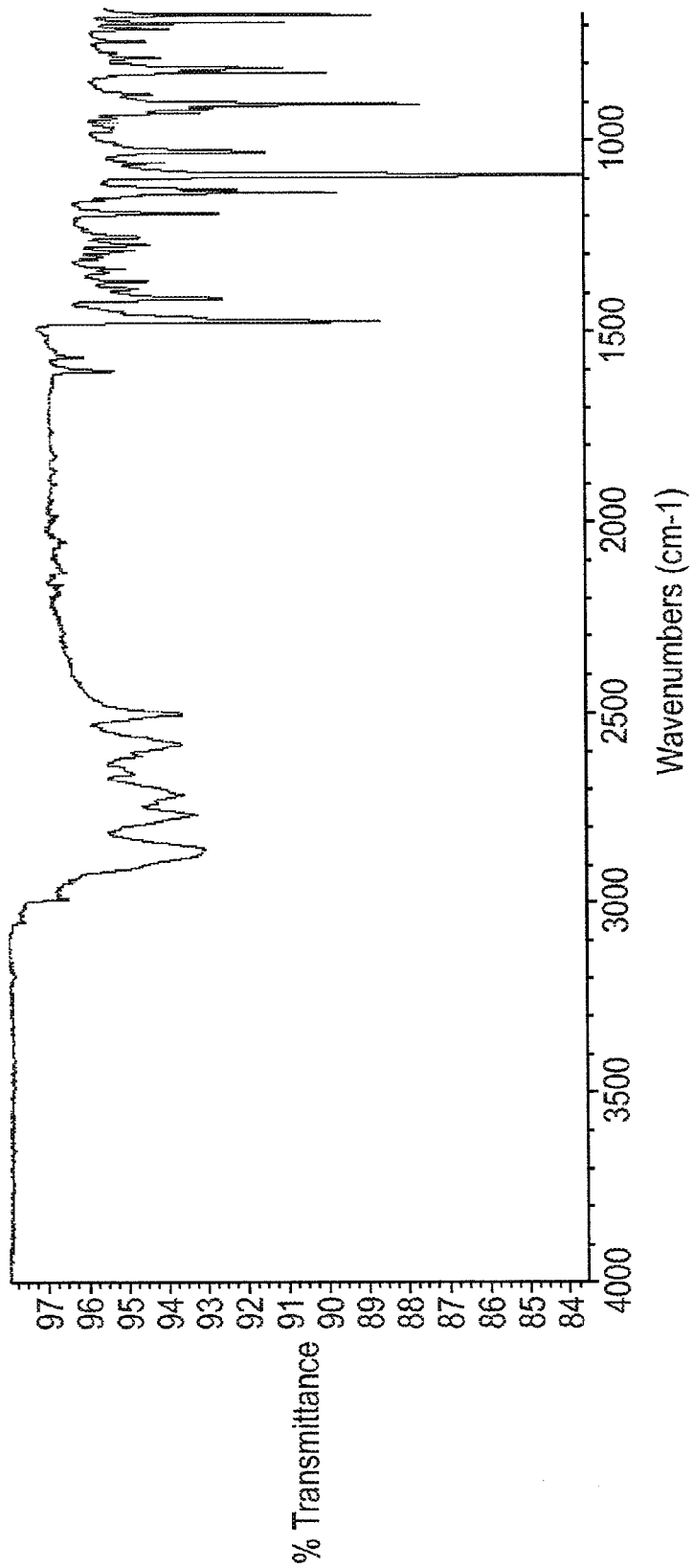

The infrared spectrum of the solid product from Example 2 (see FIG. 9) was recorded using a Perkin Elmer Spectrum One FT-IR spectrometer fitted with a Diamond/ZnSe Universal ATR Accessory at 2 cm$^{-1}$ resolution. Data were digitised at 1 cm$^{-1}$ intervals. Bands were observed at: 2858, 2767, 2715, 2657, 2581, 2503, 1603, 1564, 1472, 1411, 1385, 1368, 1336, 1286, 1272, 1251, 1191, 1137, 1125, 1090, 1058, 1028, 966, 951, 927, 914, 906, 879, 820, 808, 782, 739, 706, 692 and 669 cm$^{-1}$.

Figure 10:
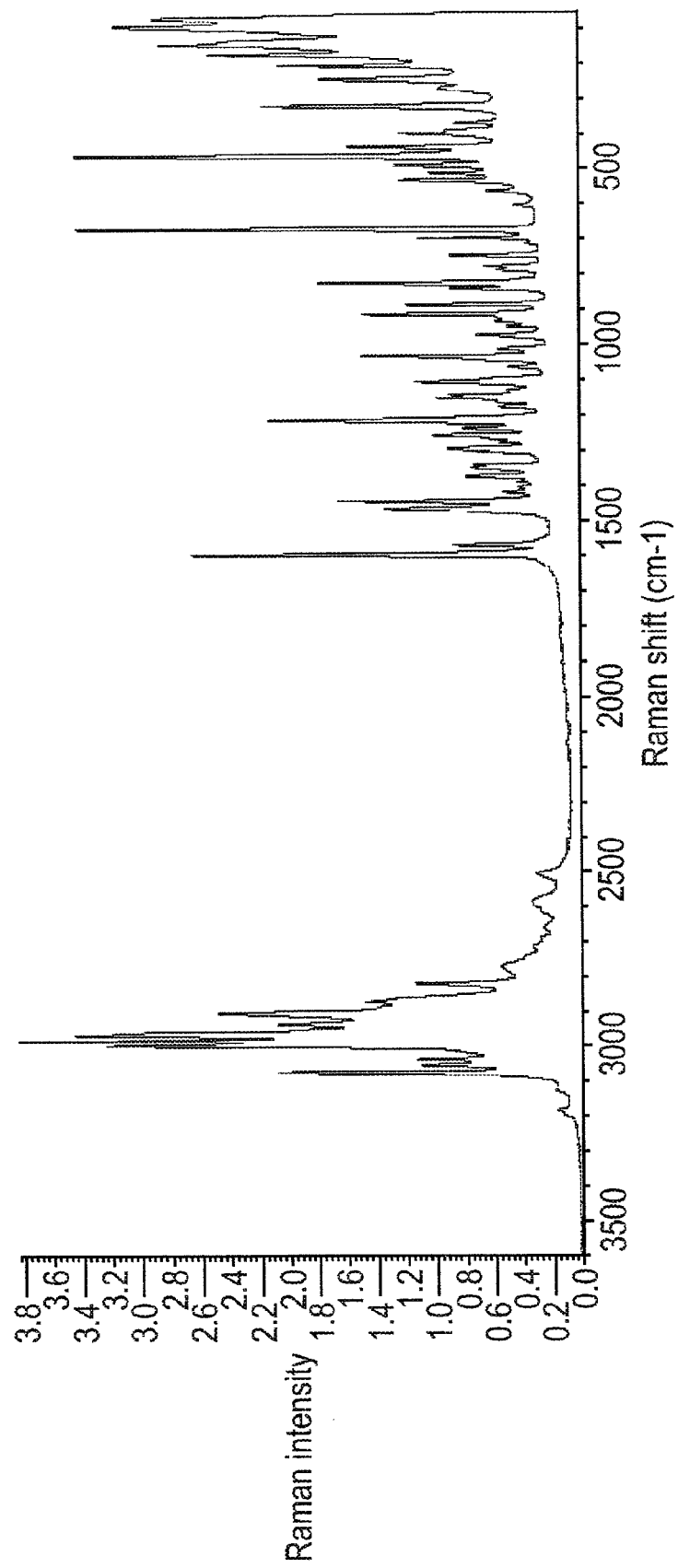

The Raman spectrum of the product from Example 2 (see FIG. 10) was recorded with the sample in an NMR tube using a Nicolet 960 E.S.P. FT-Raman spectrometer, at 4 cm$^{-1}$ resolution with excitation from a Nd:VO4 laser (1064 nm) with a power output of 400 mW. Bands were observed at: 3072, 2994, 2980, 2965, 2935, 2905, 2870, 1592, 1564, 1462, 1442, 1210, 1028, 907, 880, 820, 670, 530, 486, 460, 432, 395, 318, 240, 201, 171, 143, 94 and 68 cm$^{-1}$.

The percentage by weight of the chloride ion in the product from Example 2 was determined using ion chromatography on a DX-600 ion chromatograph using a dionex IonPac column under standard conditions. Using this apparatus, the amount of chloride ion was determined to be 10.2%. This corresponds well to the expected amount of 10.5%.

The solubility of a sample of the hydrochloride salt of the invention was determined by adding an amount of it to a volume of solvent with stirring so as to form a slurry. The slurry was stirred at 25 degC. The stirred slurry was tested at regular intervals (i.e. 1, 3, 6 and 8 days) until the concentration of the salt in solution was substantially constant. HPLC was used to determine the salt concentration in solution.

Using this methodology, the solubility of the salt of the invention after 8 days stirring at 25 degC. was measured as 438.1 mg/ml.

EXAMPLE 3

Figure 11:
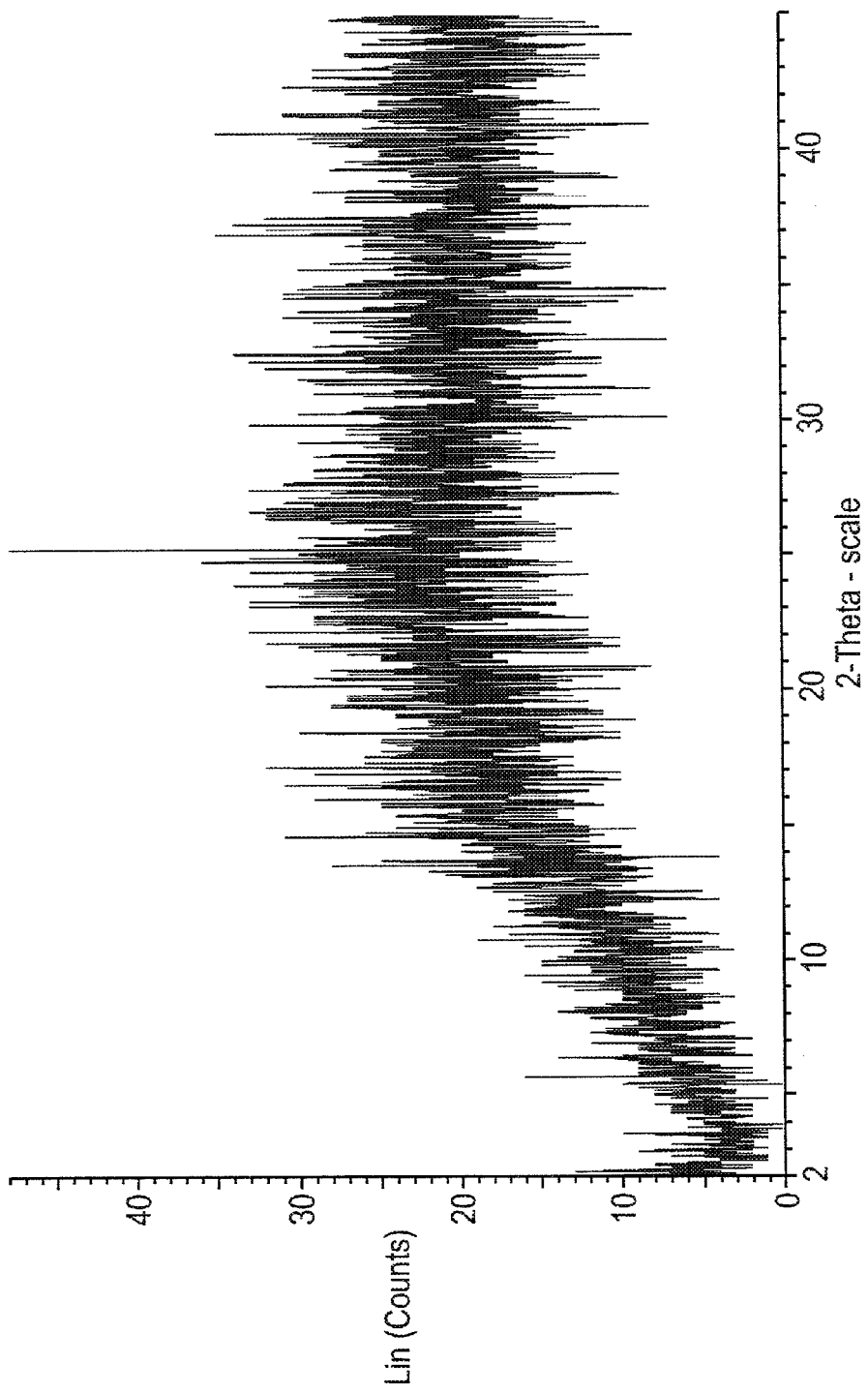
Figure 12:
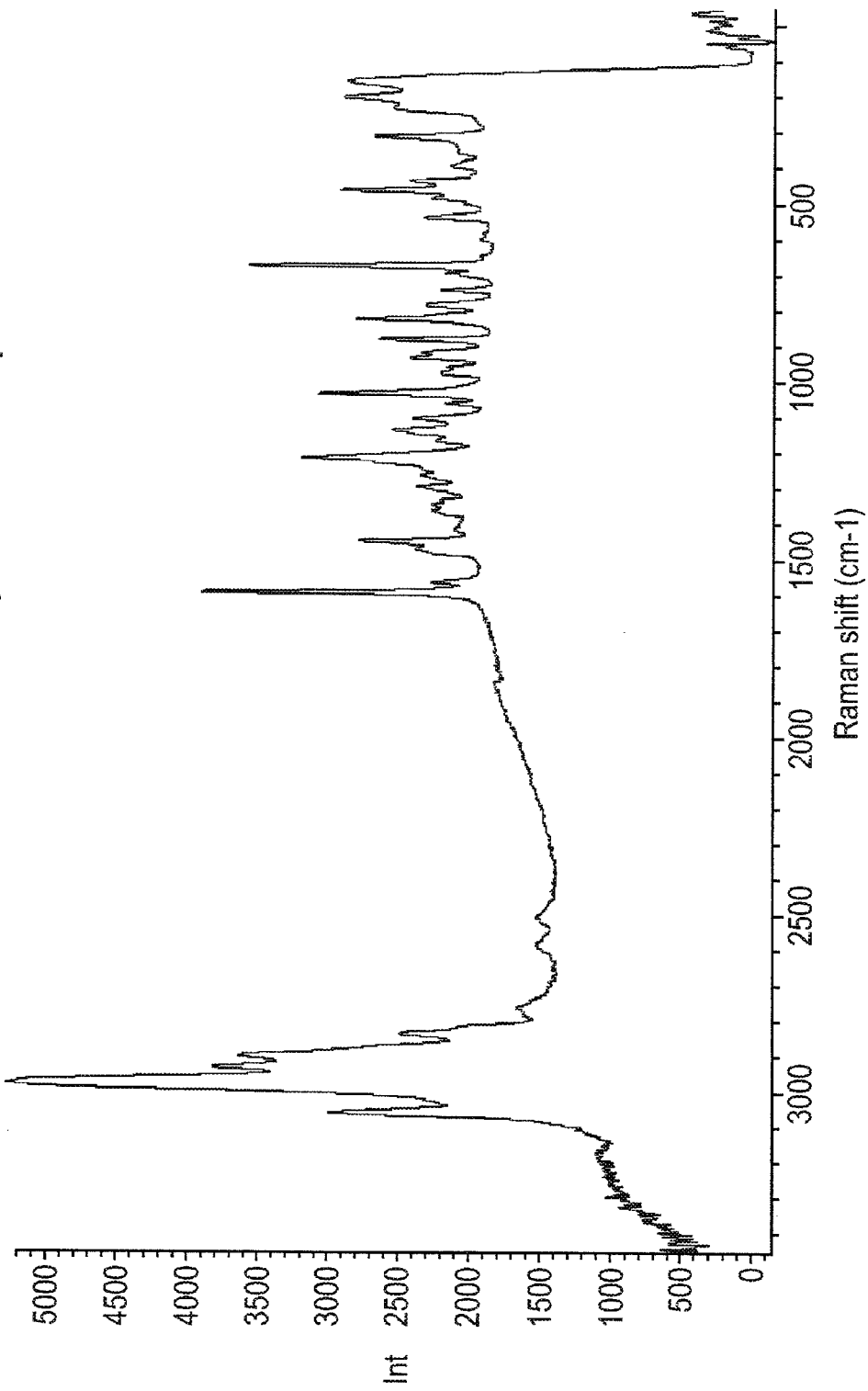

Preparation of an Amorphous Hydrochloride Salt of (1R,2R,3S,5S)-3-(3,4-dichlorophenyl)-2-[(methyloxy)methyl]-8-azabicyclo[3.2.1]octane An aluminium pan containing crystalline hydrochloride salt of (1R,2R,5S)-3-(3,4-dichlorophenyl)-2-[(methyloxy)methyl]-8-azabicyclo[3.2.1]octane (38 mg) was placed in a TGA furnace and the temperature increased at a rate of 10 degC. per minute to a final temperature of 220 degC. The temperature was maintained at 220 degC for 2 minutes and then cooled at a rate of 20 degC. per minute to 30 degC. The resulting powder was analysed by XRPD. The apparatus comprised a Bruker D5005 powder diffractometer (serial number K2-1091) using a SOL-X detector. Acquisition conditions comprised were: Radiation: Cu K; generator tension: 40 kV; generator current: 50 mA; start angle: 2.0 °2theta; end angle: 45.0 °2theta; step size: 0.02 °2theta; and time per step: 1 seconds. The sample was prepared on a zero background plate. The resulting XRPD spectrum is shown in FIG. 11. The powder was also analysed by raman spectroscopy. The apparatus comprised a Kaiser RXN-1 spectrometer operating at 785 nm wavelength. The experimental conditions were 50× objective, 200 mW laser power, 10 accumulations and 1 second exposure. The spectrometer was connected to a Leica microscope through a 62.5 μm multimode excitation fibre and the 100 μm collection fibres. The resulting raman spectrum is shown in FIG. 12.

EXAMPLE 4

Preparation of a Dosage Form of the Salt of the Invention a) Preparation of Carrier Substrate Pass microcrystalline cellulose and pregelatinized starch through a nominal 30 mesh screen, transfer the mixture to a suitable blender and blend for approximately 5 minutes. Pass magnesium stearate through a nominal 30 mesh screen, transfer to the blender and blend the entire mixture for approximately 2 minutes. The weights of material used are calculated from the percentage weights give in Table A. Compress the blend to meet the desired specifications (for example round, biconcave tablets, range in diameter from ~8 mm to ~8.8 mm) on a suitable rotary press utilizing an appropriate tabletting tool. Pass the tablets through a de-duster and metal checker. Transfer the tablets to a suitable aqueous film-coat pan and apply a film-coat to approximately 2-6% weight gain.

TABLE A

| COMPOSITION | SPECIFICATION | PERCENTAGE | FUNCTION |
| --- | --- | --- | --- |
| Microcrystalline Cellulose (Avicel PH-102) | NF or Ph. Eur. | 90% | Diluent |
| Pregelatinized Starch (Starch 1500) | NF or Ph. Eur. | 9% | Binder |
| Magnesium Stearate | NF or Ph. Eur. | 1% | Lubricant |
| | TOTAL CORE | 100% | |
| Film-Coat | | | |
| Opadry White YS-1-7003* | NC | 2-6% wt gain | Film-Coat |
| Purified Water | USP | qs* | Processing Aid |

*White is given as an example, alternative colours could be used.

b) Preparation of the Methanolic Hydroxypropylcellulose Solution

Transfer hydroxypropylcellulose to methanol and stir with a mechanical stirrer until fully dissolved. Filter the solution through a 10 micron polypropylene depth filter to clarify. Rinse the filter with additional methanol to give the desired concentration and mix until homogeneous. The amounts of material used are calculated from the percentage weights give in Table B.

TABLE B

| COMPOSITION | SPECIFICATION | % (w/v) | FUNCTION |
| --- | --- | --- | --- |
| Hydroxypropylcellulose (Klucel EF) | NF or Ph. Eur. | 5% | Excipient |
| Methanol | USP or Ph. Eur. | qs | Vehicle |
| | TOTAL | 100% | | c) Preparation of the Dosing Solution for Liquid Dose

Transfer the required quantity of the salt of the invention to a tared mixing vessel. Transfer the required weight of hydroxypropylcellulose 5% in methanol to deliver the target amount of the salt of the invention. The amounts of material used are calculated from the percentage weights give in Table C. Stir with a mechanical stirrer or sonicate until the salt of the invention is dissolved.

TABLE C

| COMPOSITION | SPECIFICATION | % (w/w) | FUNCTION |
|---|---|---|---|
| Salt of the Invention | Non Compendial | ~11.6 to 35.0% | Active |
| Hydroxy-propylcellulose (Klucel EF) 5% in Methanol | Non Compendial | qs | Vehicle |
| TOTAL | | 100% | | d) Preparation of Dosage Form

The dosage form may be prepared using the apparatus (hereinafter "the apparatus"), processes, machines and systems described in International Patent publication WO2005/123569.

Load carrier substrate into the array plates. The array plates accurately locate the substrates for further processing. Transfer the dosing solution containing the salt of the invention into a reservoir on the apparatus and connect to a high-precision, low volume positive displacement pump. Purge the air from the supply tubing and begin to pump. Adjust the pump stroke to deliver the required volume of dosing solution. In one configuration, the apparatus has an integral high-speed imaging system that images the droplets, while "in-flight", after having been dispensed by the pump. The imaging system correlates the imaged droplet volume with the weight dispensed, to confirm the delivered dose is correct. The control system of the apparatus assigns a pass/fail to the drop volume for each individual tablet.

After dispensing the droplet onto the carrier substrate, they enter a tunnel where warmed air (40-50° C., typically) evaporates the methanol, leaving the salt of the invention bound to the carrier substrate in an adherent film. The tablets then enter a zone where a second imaging system images each tablet at a characteristic wavelength range, to confirm that the dried deposit is correctly positioned on the tablet. The control system of the apparatus assigns a pass/fail for deposition location for each tablet, based on the imaging. The control system of the apparatus reviews the pass/fail status of each tablet; failed tablets are removed from the process and directed to waste. Tablets with "pass" status for both imaging systems are approved for further processing. The composition of a typical dosage form prior to coating and printing is shown in Table D.

TABLE D

| COMPOSITION | SPECIFICATION | (mg/tablet) | FUNCTION |
|---|---|---|---|
| Liquid Dose containing the salt of the invention* | Non Compendial | ~4 mg to ~10 mg*- | Active |
| Carrier substrate | Non-Compendial. | 187 mg to 230 mg** | Drug Carrier |
| TOTAL | | Varies | |

*The content of the salt of the Invention and dispensed weight of solution varies depending on the tablet strength.
**Carrier tablet weight depends upon the diameter used.

e) Addition of a Coating Over the Salt of the Invention

Transfer Opadry to water and stir with mechanical stirrer until suspended. The amounts of material used are calculated from the percentage weights give in Table E. Transfer suspension to the ink reservoir of a pad printing system. The apparatus comprises a polymeric pad and cliche with circular etched "images" to match the area to be printed on the tablets. The pad printer intermittently picks up the coating suspension and transfers the coating to the tablet to produce the finished dosage form.

TABLE E

| COMPOSITION | SPECIFICATION | % (w/v) | FUNCTION |
|---|---|---|---|
| Opadry White YS-1-7003* | NC | 10-40%* | Film Coat |
| Purified Water | USP | qs | Processing Aid |

*White is given as an example, alternative colours could be used.

f) Printing

Printing apparatus may be used to apply identifying lettering or a logo to the surface of the tablet. The apparatus comprises a polymeric pad and cliché with an etched "image" (numbers or letters) to locate the marking onto the tablet surface. In use, the pad of the apparatus intermittently picks up marking ink (such as a black Opacode™ ink) and transfers it to the tablet to mark the logo onto the finished tablet.

EXAMPLE 5

Preparation of a Orally Disintegrating Tablet (ODT) Carrier Substrate a) Preparation of ODT Carrier Substrate

Pass StarLac and Neotame through a nominal 20 mesh screen. Transfer the mixture and unsieved mint flavoring to a suitable blender and blend for approximately 10 minutes. Pass magnesium stearate through a nominal 30 mesh screen, transfer to the blender and blend the entire mixture for approximately 2 minutes. The weights of material used are calculated from the percentage weights give in Table F. Compress the blend to meet the desired specifications (for example round, biconcave tablets, range in diameter from ~8 mm to ~9.5 mm) on a suitable rotary press utilizing appropriate tablet tooling. Pass the tablets through a de-duster and metal checker.

TABLE F

| COMPOSITION | SPECIFICATION | % (w/w) | FUNCTION |
|---|---|---|---|
| StarLac* | Non Compendial | 98.5% | Diluent |
| Mint Flavoring | Non Compendial | 0.9% | Flavoring |
| Neotame | NF | 0.1% | Sweetener |
| Magnesium Stearate | Ph. Eur/USP-NF/JP | 0.5% | Lubricant |

*StarLac: mixture of 85% alpha-lactose monohydrate (Ph. Eur./USP-NF) and 15% maize starch (Ph. Eur./USP-NF)

b) Preparation of Ethylcellulose Coat for Application to Tablet by Pad-Printing Dissolve ethylcellulose in methanol with stirring, then add triethyl citrate. The weights of material used are calculated from the percentage weights give in Table G. Add sufficient methanol to bring to target on w/w basis. Transfer solution to the ink cup of a pad printing machine equipped with a suitable image cliché with a round image, slightly smaller diameter then the actual tablet diameter. Install a suitable polymer pad to match the cliché image plate. Tablets are presented to the pad printer in a defined array, matching the cliché. The pad printer will apply 2-4 tamps to the carrier tablet to apply a coat that will provide a protective layer to mitigate solvent infiltration into the uncoated carrier substrate during the liquid dispensing process.

TABLE G

| COMPOSITION | SPECIFICATION | % (w/w) | FUNCTION |
|---|---|---|---|
| Ethylcellulose | NF | 30 | Protective barrier coat |
| Triethyl Citrate | Ph. Eur./USP-NF | 1.67 | Plasticiser |
| Methanol | Ph. Eur./USP-NF | qs*** to 100 | vehicle |

***Methanol eliminated by evaporation.

EXAMPLE 6

Alternative Preparation of an Orally Disintegrating Tablet (ODT) Carrier Substrate Pass mannitol, crospovidone XL, xylitol and Neotame through a nominal 20 mesh screen, transfer the mixture and the unseived Mint Flavoring to a suitable blender and blend for approximately 10 minutes. Pass magnesium stearate and colloidal silicon dioxide through a nominal 30 mesh screen, transfer to the blender and blend the entire mixture for approximately 2 minutes. The weights of material used are calculated from the percentage weights give in Table H. Compress the blend to meet the desired specifications (for example round, biconcave tablets, range in diameter from ~8 mm to ~9.5 mm) on a suitable rotary press utilizing an appropriate tablet tooling. Pass the tablets through a de-duster and metal checker.

An ethyl ellylcellulose coat may be prepared and applied as described for Example 5

TABLE H

| COMPOSITION | SPECIFICATION | % (w/w) | FUNCTION |
|---|---|---|---|
| Mannitol (Grade 300 Direct Compression) | Ph. Eur/USP-NF/JP | 73.15% | Diluent/sweetener |
| Crospovidone XL | Ph. Eur/USP-NF | 20.00% | Disintegrant |
| Xylitol (Grade 300 for Direct Compression) | Ph. Eur/USP-NF/JP | 5.00% | Diluent/sweetener |
| Mint Flavoring | Non Compendial | 0.90% | Flavoring |
| Neotame | NF | 0.10% | Sweetener |
| Magnesium Stearate | Ph. Eur/USP-NF/JP | 0.75% | Lubricant |
| Colloidal silicon dioxide | Ph. Eur/USP-NF/JP | 0.10% | Lubricant |

The invention claimed is:

1. A crystalline anhydrate hydrochloride salt of (1R,2R,3S,5S)-2-methoxymethyl-3-(3,4-dichlorophenyl)-8-azabicyclo[3.2.1]octane, which salt has the crystal structure characterized by the following XRPD peak list:

| Position (±0.2 °2theta) | d-spacing (Angstroms) |
|---|---|
| 6.2 | 14.2 |
| 12.5 | 7.1 |
| 13.5 | 6.6 |
| 15.6 | 5.7 |
| 18.7 | 4.8. |

2. The hydrochloride salt according to claim 1, which salt has the crystal structure characterized by the following XRPD peak list:

| Position (±0.2 °2theta) | d-spacing (angstroms) |
|---|---|
| 6.2 | 14.2 |
| 12.5 | 7.1 |
| 13.1 | 6.7 |
| 13.5 | 6.6 |
| 15.6 | 5.7 |
| 16.9 | 5.2 |
| 18.7 | 4.8 |
| 21.7 | 4.1 |
| 22.0 | 4.0 |
| 22.5 | 3.9 |
| 22.8 | 3.9 |
| 24.0 | 3.7 |
| 24.9 | 3.6 |
| 25.1 | 3.5 |
| 25.6 | 3.5 |
| 26.1 | 3.4 |
| 26.7 | 3.3 |
| 27.1 | 3.3 |
| 28.0 | 3.2 |
| 29.9 | 3.0. |

3. The hydrochloride salt according to claim 2, which salt has the crystal structure characterized by the XRPD spectrum substantially the same as in FIG. 1.

4. A crystalline anhydrate hydrochloride salt of (1R,2R,3S,5S)-2-methoxymethyl-3-(3,4-dichlorophenyl)-8-azabicyclo[3.2.1]octane, having the crystal structure characterized by a melting endotherm with an onset of 211±3° C. in the DSC thermogram.

5. A crystalline anhydrate hydrochloride salt of (1R,2R,3S,5S)-2-methoxymethyl-3-(3,4-dichlorophenyl)-8-azabicyclo[3.2.1]octane, having the crystal structure characterized by the following absorption peaks in the infrared spectrum of the solid product at 2858, 2767, 2715, 2581, 2503, 1472, 1411, 1368, 1272, 1191, 1137, 1125, 1090, 1058, 1028, 927, 914, 906, 879, 820, 808, 782, 706, 692 and 669±4 cm$^{-1}$.

6. The hydrochloride salt according to claim 5, having the crystal structure characterized by the following absorption peaks in the infrared spectrum of the solid product at 2858, 2767, 2715, 2657, 2581, 2503, 1603, 1564, 1472, 1411, 1385, 1368, 1336, 1286, 1272, 1251, 1191, 1137, 1125, 1090, 1058, 1028, 966, 951, 927, 914, 906, 879, 820, 808, 782, 739, 706, 692 and 669±4 cm$^{-1}$.

7. The hydrochloride salt according to claim 6, having the crystal structure characterized in that it has an infrared spectrum substantially the same as in FIG. 4.

8. A crystalline anhydrate hydrochloride salt of (1R,2R,3S,5S)-2-methoxymethyl-3-(3,4-dichlorophenyl)-8-azabicyclo[3.2.1]octane, having the crystal structure characterized by the following peaks in the Raman spectrum at 3072, 2994, 2980, 2965, 2935, 2905, 2870, 1592, 1462, 1442, 1210, 1028, 907, 880, 820, 670, 530, 486, 460, 432, 395, 318, 240, 201, 171, 143, 94 and 68±4 cm$^{-1}$.

9. The hydrochloride salt according to claim 8, having the crystal structure characterized in that it has a Raman spectrum substantially the same as in FIG. 5.

10. A method for making a dosage form of the hydrochloride salt according to any one of claim 1, 4, 5, or 8, the method comprising:
   a) adding a metered liquid dose onto each of a plurality of carrier substrates; the liquid dose comprising a hydrochloride salt of (1R,2R,3S,5S)-2-methoxymethyl-3-(3,4-dichlorophenyl)-8-azabicyclo[3.2.1]octane dissolved in a suitable solvent system;
   b) evaporating the solvent; and
   c) optionally providing a coating over the salt.

11. The hydrochloride salt according to any one of claim 1, 4, 5, or 8 dissolved in a solvent system.

12. A liquid dose comprising the hydrochloride salt according to claim 11.

13. A pharmaceutical dosage form obtained by the method defined in claim 10.

14. A pharmaceutical dosage form comprising a carrier substrate and the hydrochloride salt according to any one of claim 1, 4, 5, or 8.

* * * * *